United States Patent
Pan et al.

(10) Patent No.: US 10,779,772 B2
(45) Date of Patent: Sep. 22, 2020

(54) MOVEMENT ASSESSING METHOD AND SYSTEM

(71) Applicant: INDUSTRIAL TECHNOLOGY RESEARCH INSTITUTE, Hsinchu (TW)

(72) Inventors: Hsin-Hung Pan, Luodong Township, Yilan County (TW); Jung-Hao Wang, New Taipei (TW); Guan-Ting Chen, Kaohsiung (TW); Yao-Hsien Huang, Taipei (TW); Hsien-Te Peng, Taipei (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 372 days.

(21) Appl. No.: 15/802,728

(22) Filed: Nov. 3, 2017

(65) Prior Publication Data
US 2018/0140259 A1 May 24, 2018

Related U.S. Application Data

(60) Provisional application No. 62/416,744, filed on Nov. 3, 2016.

(51) Int. Cl.
*A61B 5/00* (2006.01)
*A61B 5/11* (2006.01)
*A61B 5/107* (2006.01)

(52) U.S. Cl.
CPC .......... *A61B 5/7278* (2013.01); *A61B 5/0036* (2018.08); *A61B 5/1071* (2013.01);
(Continued)

(58) Field of Classification Search
CPC ... A61B 5/7278; A61B 5/1071; A61B 5/4836; A61B 5/11; A61B 2505/09;
(Continued)

(56) References Cited

U.S. PATENT DOCUMENTS 4,813,436 A 3/1989 Au
6,280,361 B1 8/2001 Harvey et al.
(Continued)

FOREIGN PATENT DOCUMENTS

CN 103620607 A 3/2014
CN 104083174 A 10/2014
(Continued)

OTHER PUBLICATIONS

Chinese Office Action and Search Report for Chinese Application No. 201711071075.9, dated Apr. 19, 2019.
(Continued)

*Primary Examiner* — Eric F Winakur
*Assistant Examiner* — Abid A Mustansir
(74) *Attorney, Agent, or Firm* — Birch, Stewart, Kolasch & Birch, LLP (57) ABSTRACT

A movement assessing method and a movement assessing system are provided. The movement assessing method includes the following steps. At least one limb angle is obtained. A limb position accuracy is analyzed according to the limb angle. A center of gravity is obtained. A balance accuracy is analyzed according to the center of gravity. A movement index is calculated via a limb weight and a balance weight according to at least the limb position accuracy and the balance accuracy.

20 Claims, 9 Drawing Sheets

(52) U.S. Cl.
CPC .............. *A61B 5/11* (2013.01); *A61B 5/4836* (2013.01); *A61B 2505/09* (2013.01)

(58) Field of Classification Search
CPC .............. A61B 5/1114; A63B 2230/62; A63B 2220/24; A63B 2220/20; A63B 2220/13; A63B 71/0605
See application file for complete search history.

(56) References Cited

U.S. PATENT DOCUMENTS

| | | | |
|---|---|---|---|
| 6,876,496 | B2 | 4/2005 | French et al. |
| 7,553,266 | B2 | 6/2009 | Abdoli-Eramaki |
| 8,437,844 | B2 | 5/2013 | Syed Momen et al. |
| 8,540,649 | B2 | 9/2013 | Kurata et al. |
| 8,608,623 | B2 | 12/2013 | Lee |
| 8,620,146 | B1 | 12/2013 | Coleman |
| 8,840,629 | B2 | 9/2014 | Bonutti |
| 8,979,722 | B2 | 3/2015 | Klein et al. |
| 9,011,293 | B2 | 4/2015 | Shavit et al. |
| 9,125,620 | B2 | 9/2015 | Walke et al. |
| 9,289,674 | B2 | 3/2016 | Winsper et al. |
| 9,350,951 | B1 | 5/2016 | Rowe |
| 9,403,056 | B2 | 8/2016 | Weinberg et al. |
| 9,421,141 | B2 | 8/2016 | Bose et al. |
| 9,470,763 | B2 | 10/2016 | Solinsky |
| 9,486,692 | B2 | 11/2016 | Crowley et al. |
| 9,489,863 | B2 | 11/2016 | Ellis |
| 2008/0204225 | A1 | 8/2008 | Kitchen |
| 2009/0299232 | A1 | 12/2009 | Lanfermann et al. |
| 2010/0312148 | A1 | 12/2010 | Sato |
| 2011/0112771 | A1 | 5/2011 | French |
| 2012/0130280 | A1 | 5/2012 | Lee |
| 2012/0183940 | A1 | 7/2012 | Aragones et al. |
| 2013/0123645 | A1* | 5/2013 | Stimson ................ A61B 5/1118 600/476 |
| 2013/0171601 | A1* | 7/2013 | Yuasa ................... A61B 5/1114 434/258 |
| 2014/0032162 | A1 | 1/2014 | Papadourakis |
| 2014/0058291 | A1 | 2/2014 | Wartell et al. |
| 2014/0220527 | A1 | 8/2014 | Li et al. |
| 2014/0278125 | A1 | 9/2014 | Balakrishnan et al. |
| 2016/0081051 | A1 | 3/2016 | Kim et al. |

FOREIGN PATENT DOCUMENTS

| | | | | |
|---|---|---|---|---|
| CN | 104190065 | A | 12/2014 | |
| CN | 105380652 | A | 3/2016 | |
| CN | 105581799 | A | 5/2016 | |
| TW | 201113005 | A | 4/2011 | |
| TW | 201501752 | A | 1/2015 | |
| TW | I468198 | B | 1/2015 | |
| TW | M505953 | U | 8/2015 | |
| TW | I509556 | B | 11/2015 | |
| WO | WO-2012082782 | A1 * | 6/2012 | ......... A63B 71/0622 |

OTHER PUBLICATIONS

Chiba et al., "Human Upright Posture Control Models Based on Multisensory Inputs; In Fast and Slow Dynamics," Neuroscience Research, vol. 104, 2016 (Available online Dec. 30, 2015), pp. 96-104.

Griškevičius et al., "Evaluation of Human Postural Balance in Quiet Standing by Direct Measurement of Human Body Center of Mass Acceleration," Journal of Vibroengineering. vol. XX, Issue X, Mar. 2009, pp. 1-6.

Kritz et al., "The Bodyweight Squat: A Movement Screen for the Squat Pattern," National Strength and Conditioning Association, vol. 31, No. 1, Feb. 2009, pp. 76-85.

Kuo, "An Optimal Control Model for Analyzing Human Postural Balance," IEEE Transactions on Biomedical Engineering, vol. 42, No. 1, Jan. 1, 1995, pp. 87-101.

Oliveira et al., "Calculation of Area of Stabilometric Signals Using Principal Component Analysis," Physiol. Meas, vol. 17, 1996, pp. 305-312 (Total 9 pages).

Xia et al., "Human Detection Using Depth Information by Kinect," Computer Vision and Pattern Recognition Workshops (CVPRW), 2011 IEEE Computer Society Conference on, Colorado Springs, USA, Jun. 20-25, 2011, pp. 15-22 (Total 9 pages).

Taiwanese Office Action and Search Report for Taiwanese Application 106138027, dated Dec. 13, 2018.

* cited by examiner

MOVEMENT ASSESSING METHOD AND SYSTEM

This application claims the benefit of U.S. provisional application Ser. No. 62/416,744, filed Nov. 3, 2016, the subject matter of which is incorporated herein by reference.

BACKGROUND OF THE INVENTION

Field of the Invention

The invention relates in general to a movement assessing method and system, and more particularly to a method and system for assessing the posture of limb exercise.

Description of the Related Art

Suitable exercises help people to maintain the health of mind and body. Moreover, exercises can help the patients with their rehabilitation. However, exercises must be performed according to correct postures so that desired effect can be achieved. On the contrary, incorrect postures may cause harm to the body.

To correct the postures of exercises, people normally have a coach or a physiotherapist to instantly remind them of their postures of exercises. However, when the coach or the physiotherapist is not there, people may not be able to perform correct exercises, the effect of exercises will be greatly reduced.

SUMMARY OF THE INVENTION

The invention is directed to a movement assessing method and a movement assessing system.

According to one embodiment of the invention, a movement assessing method is provided. The movement assessing method includes the following steps. At least one limb angle is obtained. A limb position accuracy is analyzed according to the limb angle. A center of gravity is obtained. Balance accuracy is analyzed according to the center of gravity. A movement index is calculated via a limb weight and a balance weight according to at least the limb position accuracy and the balance accuracy.

According to another embodiment of the invention, a movement assessing system is provided. The movement assessing system includes an angle arithmetic unit, a limb analysis unit, a center of gravity arithmetic unit, a balance analysis unit and an index calculation unit. The angle arithmetic unit is for obtaining at least one limb angle. The limb analysis unit is for analyzing a limb position accuracy according to the limb angle. The center of gravity arithmetic unit is for obtaining a center of gravity. The balance analysis unit is for analyzing a balance accuracy according to the center of gravity. The index calculation unit is for calculating a movement index via a limb weight and a balance weight according to at least the limb position accuracy and the balance accuracy.

The above and other aspects of the invention will become better understood with regard to the following detailed description of the preferred but non-limiting embodiment(s). The following description is made with reference to the accompanying drawings.

DETAILED DESCRIPTION OF THE INVENTION

Figure 1:
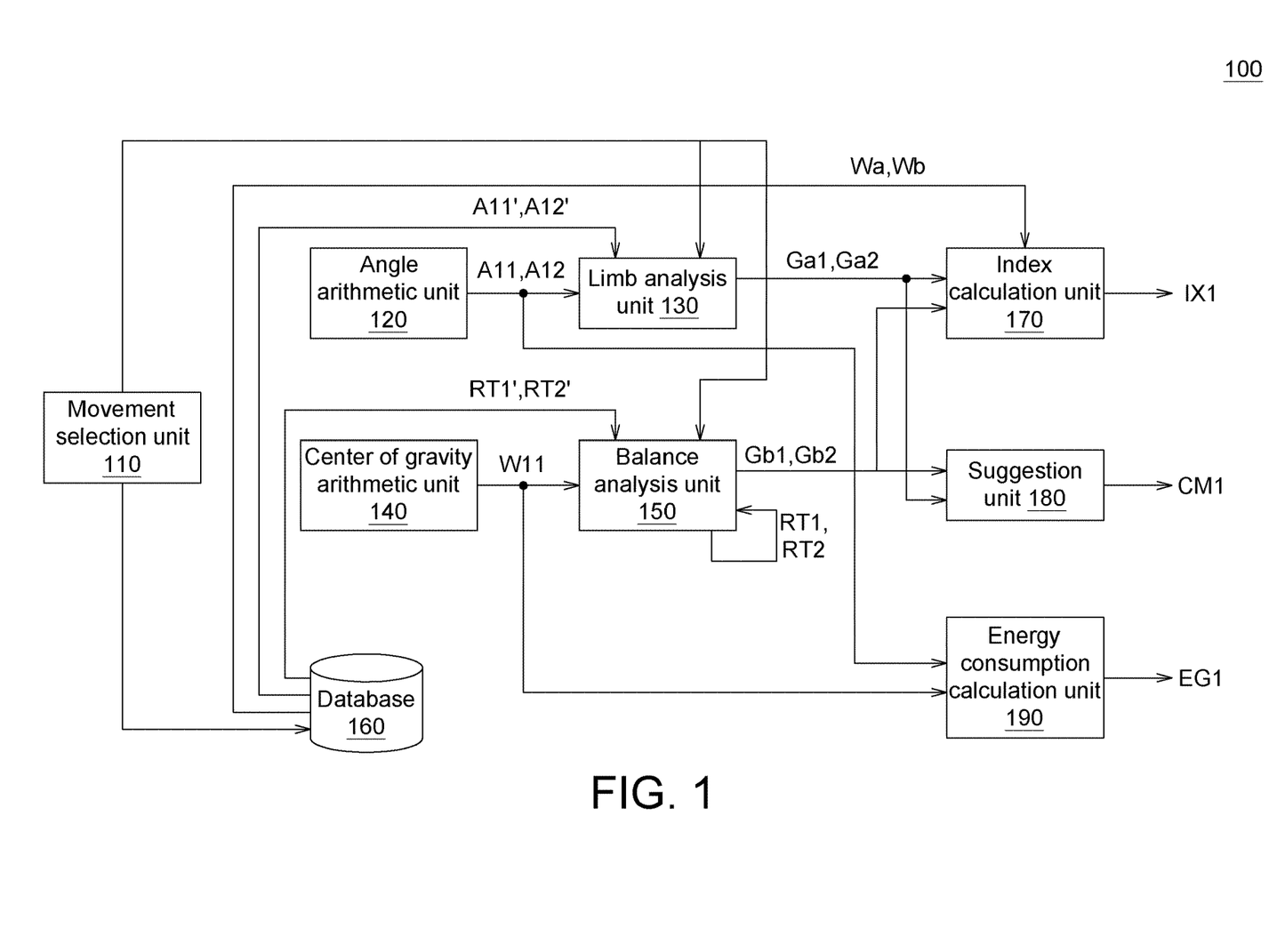
FIG. 1 is a schematic diagram of a movement assessing system according to an embodiment.

Referring to FIG. 1, a schematic diagram of a movement assessing system 100 according to an embodiment is shown. The movement assessing system 100 can instantly evaluate exercise postures to provide suitable suggestions or warnings. Thus, even in the absence of a coach or physiotherapist, a person still can do exercise with correct and safe postures.

The movement assessing system 100 includes a movement selection unit 110, an angle arithmetic unit 120, a limb analysis unit 130, a center of gravity arithmetic unit 140, a balance analysis unit 150, a database 160, an index calculation unit 170, a suggestion unit 180 and an energy consumption calculation unit 190. The movement selection unit 110 is for a subject to select a desired exercise. The angle arithmetic unit 120 and the center of gravity arithmetic unit 140 are for obtaining the feature of the movement performed by the subject. The angle arithmetic unit 120 can be realized by an infrared camera, a gyroscope or an ultrasonic sensor. The center of gravity arithmetic unit 140 can be realized by a spring pressure sensor, a pressure sensor or a piezoelectric element.

The limb analysis unit 130 and the balance analysis unit 150 further check movement accuracy of the subject according to the standard data of the exercise. The index calculation unit 170 is for calculating an integrated index. The limb analysis unit 130, the balance analysis unit 150 and the index calculation unit 170 can be realized by a chip, a circuit board, a circuit or a computer-readable recording medium storing a plurality of program codes.

The suggestion unit 180 is for providing suggestions to the subject. The suggestion unit 180 can be realized by a speaker, a monitor, a warning light or a warning vibration. The energy consumption calculation unit 190 is for calculating the energy consumed by the subject, and can be realized by a chip, a circuit board, a circuit or a computer-readable recording medium storing a plurality of program codes.

Figure 2:
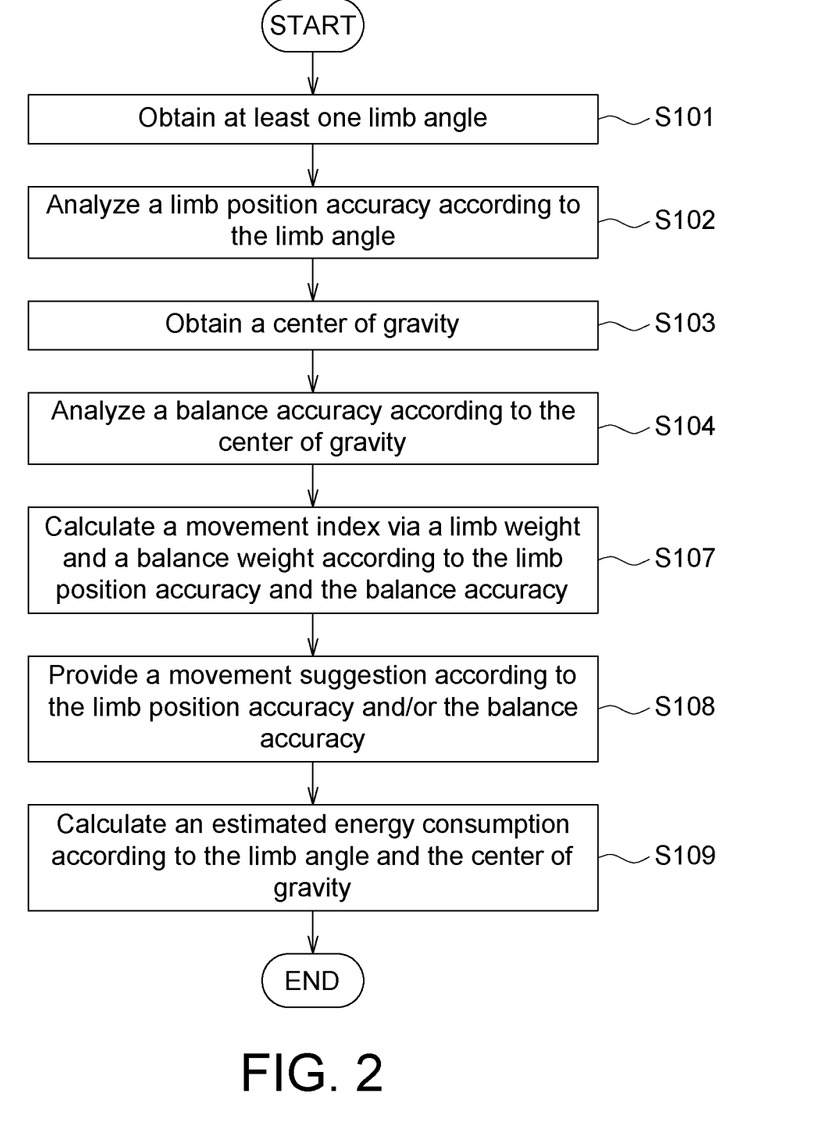
FIG. 2 is a flowchart of a movement assessing method according to an embodiment.
Figure 3:
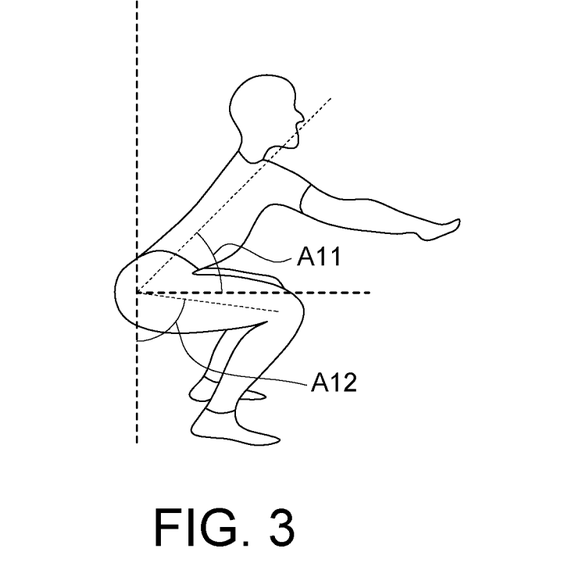
FIG. 3 is a schematic diagram of the limb position of a subject performing a squat exercise.

Operations of the above elements are described below with a flowchart. Referring to FIG. 2, a flowchart of a movement assessing method according to an embodiment is shown. Firstly, the subject selects a desired exercise, such as squat or bench press, through the movement selection unit 110. Refer to FIG. 3 and Table 1. FIG. 3 is a schematic diagram of the limb position of a subject performing a squat exercise. In step S101, the angle arithmetic unit 120 obtains at least limb angles A11 and A12. In this step, the angle arithmetic unit 120 obtains the limb angles A11 and A12 through a depth sensor, a gyro or other suitable devices. The limb angle A11 is an angle between a back torso and a horizontal line of the ground. The limb angle A12 is an angle between a thigh segment and a vertical line of the ground. In another embodiment, only one limb angle is calculated, and the limb angle can also be an angle between a limb and the ground or between two limbs.

TABLE 1

| Limb angle | Suggested range of limb angle | Limb position accuracy | Movement suggestion | |
|---|---|---|---|---|
| A11 | Suggested range of limb angle A11': 50-70° | Ga1 | >70 | The trunk is too upright and needs to lean forward. |
| | | | <50 | The trunk leans forward too much and needs to be leans forward less. |
| A12 | Suggested range of limb angle A12': 80-100° | Ga2 | >100 | The squat is too deep and the subject needs to reduce the squat depth. |
| | | | <80 | The squat is too shallow and the subject needs to increase the squat depth. |

Then, the method proceeds to step S102, the limb analysis unit 130 analyzes limb position accuracy Ga1 and Ga2 according to the limb angles A11 and A12. In this step, the movement selection unit 110 selects a suggested range of limb angle A11', such as 50-70°, and a suggested range of limb angle A12', such as 80-100', from the database 160 according to the exercise selected by the subject. The limb analysis unit 130 checks whether the limb angles A11 and A12 fall within the suggested ranges of limb angles A11' and A12'. If the limb angles A11 and A12 fall within the suggested ranges of limb angles A11' and A12', the limb position accuracy Ga1 and Ga2 respectively have 100 marks. If the limb angles A11 and A12 are outside the suggested range of limb angles A11' and A12', the limb position accuracy Ga1 and Ga2 are progressively decreased according to the magnitude of deviation.

Figure 4:
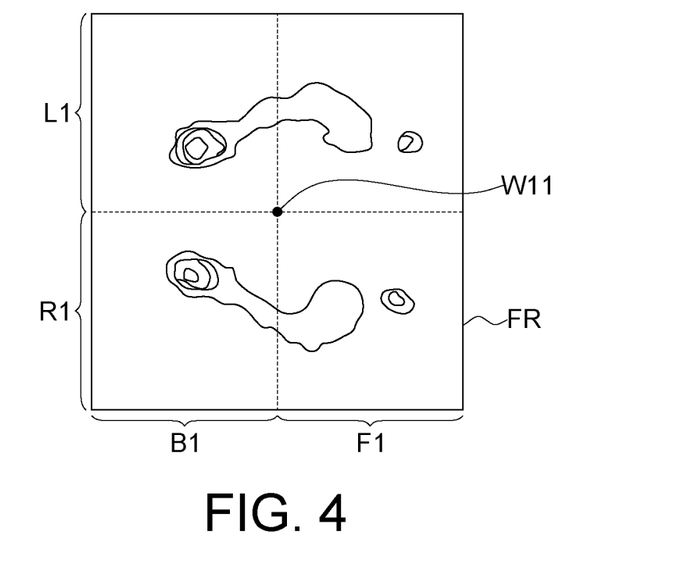
FIG. 4 is a distribution diagram of foot pressure of a subject performing a squat exercise.

Refer to FIG. 4 and Table 2. FIG. 4 is a distribution diagram of foot pressure of a subject performing a squat exercise. In step S103 as indicated in FIG. 4, the center of gravity arithmetic unit 140 obtains a center of gravity W11. In this step, the center of gravity arithmetic unit 140 can calculate the coordinate of the subject's center of gravity W11 through a spring pressure sensor, a pressure sensor or a piezoelectric element.

TABLE 2

| Front-and-back ratio/left-and-right ratio | Suggested range of front-and-back ratio/left-and-right ratio | Balance accuracy | Movement suggestion | |
|---|---|---|---|---|
| Front-and-back ratio RT1 | Suggested range of front-and-back ratio RT1': 0.8-1.2 | Gb1 | <0.8 | The body center of gravity is forward too much and needs to move backward. |
| | | | >1.2 | The body center of gravity is backward too much and needs to move forward. |
| Left-and-right ratio RT2 | Suggested range of left-and-right ratio RT2': 0.8-1.2 | Gb2 | <0.8 | The body center of gravity is rightward too much and needs to move leftward. |
| | | | >1.2 | The body enter of gravity is leftward too much and needs to move rightward. |

Then, the method proceeds to step S104, the balance analysis unit 150 analyzes balance accuracy Gb1 and Gb2 according to the center of gravity W11. In this step, the balance analysis unit 150 analyzes relative position of the center of gravity W11 as in the standard frame FR. For example, the balance analysis unit 150 calculates a front-and-back ratio RT1 between the front portion F1 and the back portion B1 divided according to the center of gravity W11 and calculates a left-and-right ratio RT2 between a left portion L1 and a right portion R1 divided according to the center of gravity W11. In this step, the movement selection unit 110 selects a suggested range of front-and-back ratio RT1', such as 0.8-1.2, and a suggested range of left-and-right ratio RT2', such as 0.8-1.2, from the database 160 according to the exercise selected by the subject. The balance analysis unit 150 checks whether the front-and-back ratio RT1 falls within the suggested range of front-and-back ratio RT1'. If yes, the balance accuracy Gb1 has 100 marks; otherwise, the balance accuracy Gb1 is progressively decreased according to the magnitude of deviation. Similarly, the balance analysis unit 150 checks whether the left-and-right ratio RT2 falls within the suggested range of left-and-right ratio RT2'. If yes, the balance accuracy Gb2 has 100 marks; otherwise, the balance accuracy Gb2 is progressively decreased according to the magnitude of deviation.

Then, the method proceeds to step S107, the index calculation unit 170 calculates a movement index IX1 via a limb weight Wa and a balance weight Wb according to the limb position accuracy Ga1 and Ga2 and the balance accuracy Gb1 and Gb2. The sum of the limb weight Wa and the balance weight Wb is equivalent to 1. In this step, the movement selection unit 110 selects the limb weight Wa and the balance weight Wb from the database 160 according to the exercise selected by the subject, and calculates the movement index IX1 according to formula (1). The limb weight Wa and the balance weight Wb are obtained according to the gender, the age or the movement type of the subject, and different limb weights Wa and balance weights Wb can be assigned to different genders, ages or movement types.

$$IX1 = Wa \times Ga1 + Wa \times Ga2 + Wb \times Gb1 + Wb \times Gb2 \tag{1}$$

Then, the method proceeds to step S108, the suggestion unit 180 provides a movement suggestion CM1 according to the limb position accuracy Ga1 and Ga2 and/or the balance accuracy Gb1 and Gb2. For example, to simply check the correctness of a posture, the suggestion unit 180 provides a movement suggestion CM1 according to the limb position accuracy Ga1 and Ga2 only. To simply check the wobbling of the center of gravity, the suggestion unit 180 provides a movement suggestion CM1 according to the balance accuracy Gb1 and Gb2 only. To simply check the accuracy of the force applied during exercise and related movement, the suggestion unit 180 provides a movement suggestion CM1 according to the limb position accuracy Ga1 and Ga2 as well as the balance accuracy Gb1 and Gb2. The contents of the movement suggestion CM1 are disclosed in Table 1 and Table 2.

Then, the method proceeds to step S109, the energy consumption calculation unit 190 calculates an estimated energy consumption EG1 according to the limb angles A11 and A12 and the center of gravity W11.

The step sequence of the assessing method is not limited to that exemplified in the flowchart of FIG. 2. For example, steps S101 and S103 can be performed concurrently, steps S102 and S104 can also be performed concurrently, and step S109 can be omitted.

Based on the above embodiments, in the absence of the coach or the physiotherapist, the subject still can obtain correct instructions of exercise and accordingly perform effective and safe autonomous exercise or self-rehabilitation.

Figure 5:
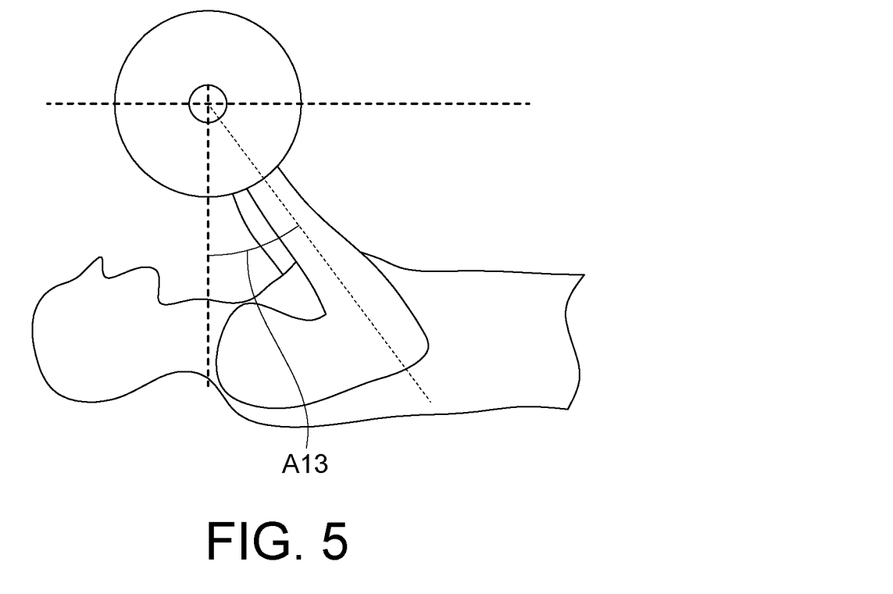
FIG. 5 is a schematic diagram of the limbs of a subject performing a bench press exercise.
Figure 6:
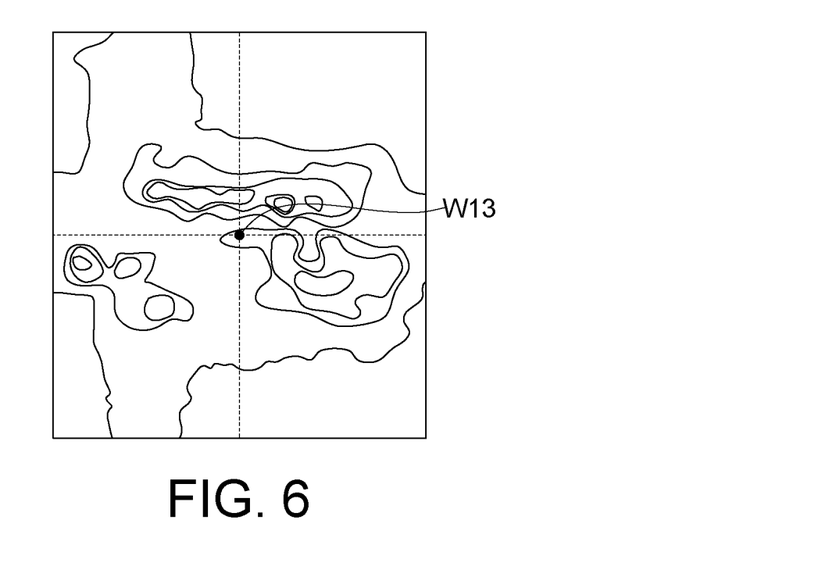
FIG. 6 is a distribution diagram of back pressure of a subject performing a bench press exercise.

Refer to FIG. 5 and FIG. 6. FIG. 5 is a schematic diagram of the limbs of a subject performing a bench press exercise. FIG. 6 is a distribution diagram of back pressure of a subject performing a bench press exercise. Let the bench press be taken for example. The angle arithmetic unit 120 obtains a limb angle A13, and then analyzes a limb position accuracy (not illustrated) according to the limb angle A13. The limb angle A13 is an angle between a forearm segment and a vertical line of the ground. The center of gravity arithmetic unit 140 obtains a center of back gravity W13 and then analyzes a balance accuracy (not illustrated) according to the center of gravity W13.

Figure 7:
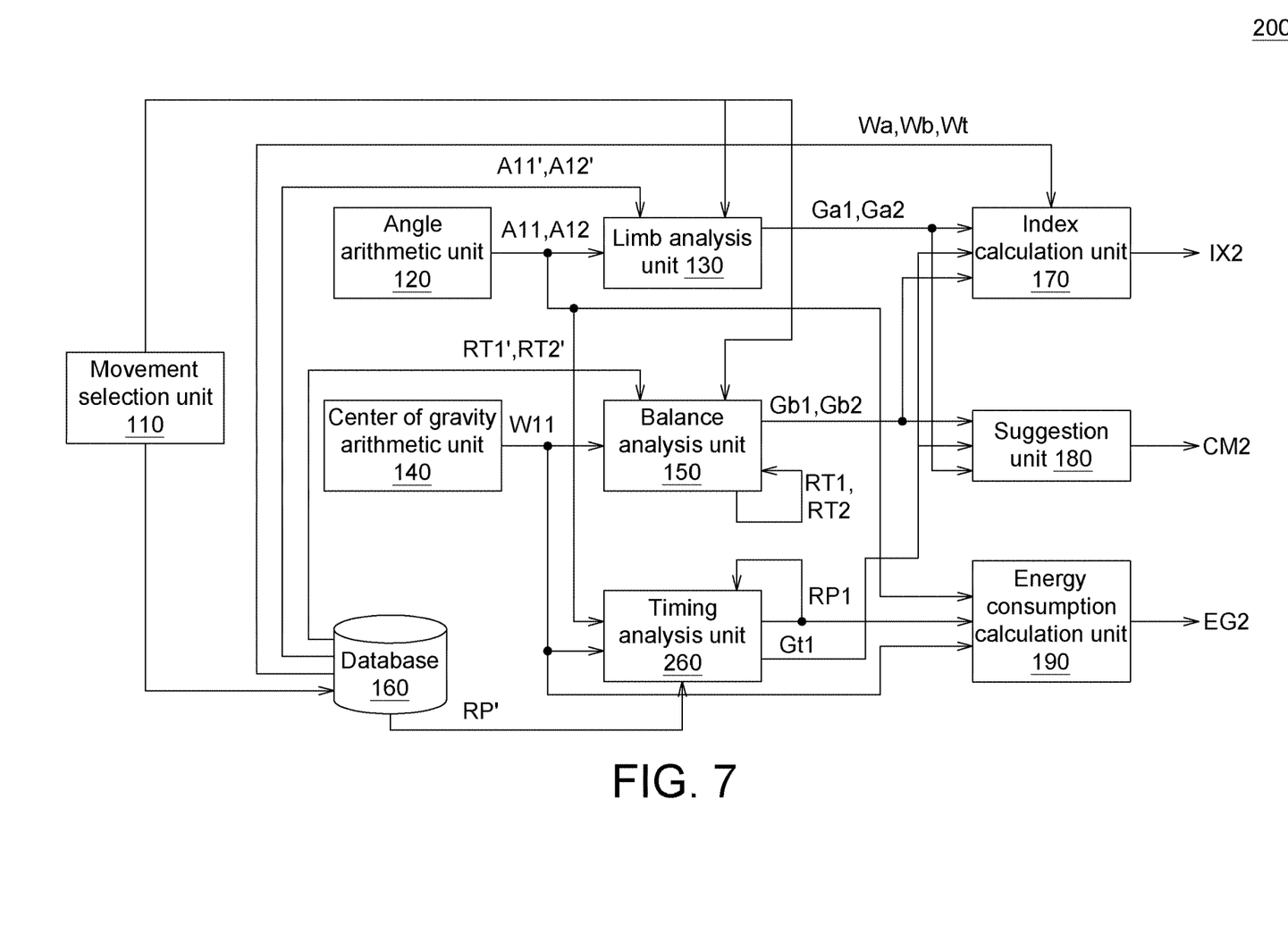
FIG. 7 is a according to another embodiment schematic diagram of a movement assessing system.

Referring to FIG. 7, a schematic diagram of a movement assessing system 200 according to another embodiment is shown. When the subject is doing exercise, the time point of movement change must be correct so that the effect of exercise can be achieved. In another embodiment, the movement assessing system 200 may further perform continuous timing analysis to provide suggestions or warnings regarding dynamic movement change during exercise. The movement assessing system 200 may further include a timing analysis unit 260 for checking the correctness of movement change of the subject. The timing analysis unit 260 can be realized by a chip, a circuit board, a circuit or a computer-readable recording medium storing a plurality of program codes.

Figure 8:
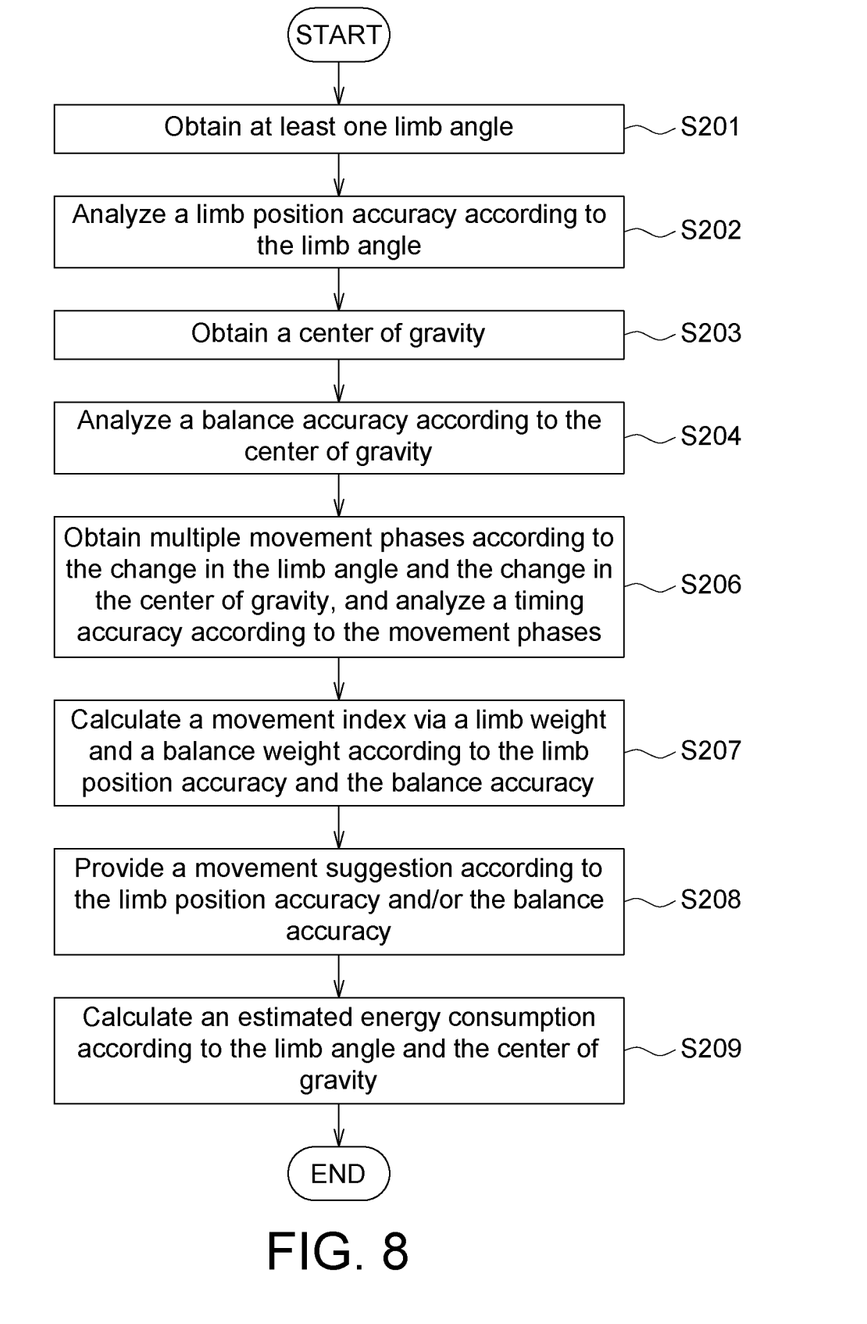
FIG. 8 is a flowchart of a movement assessing method according to another embodiment.
Figure 9:
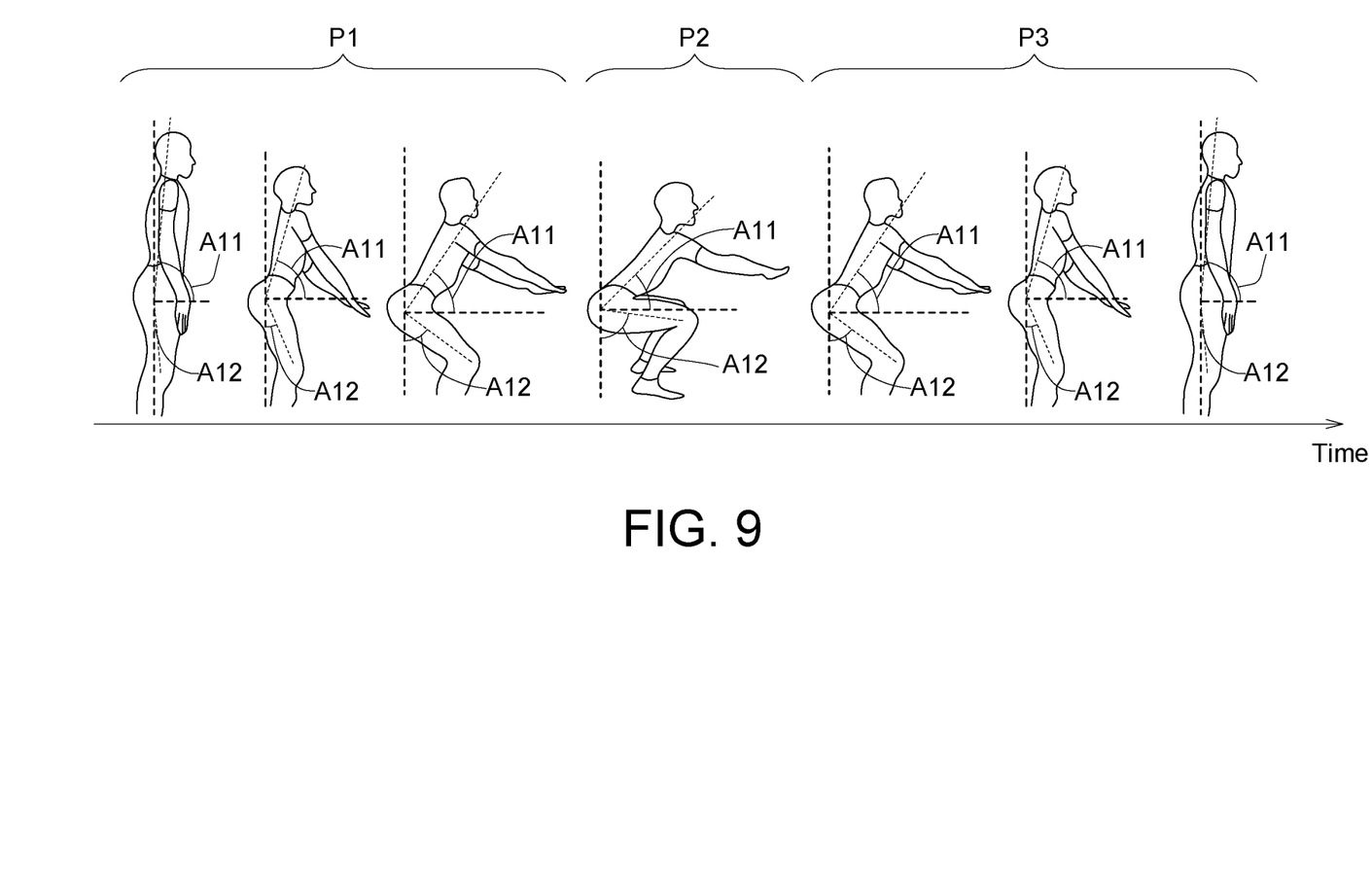
FIG. 9 is a diagram showing continuous changes of a subject performing a squat exercise.
Figure 10:
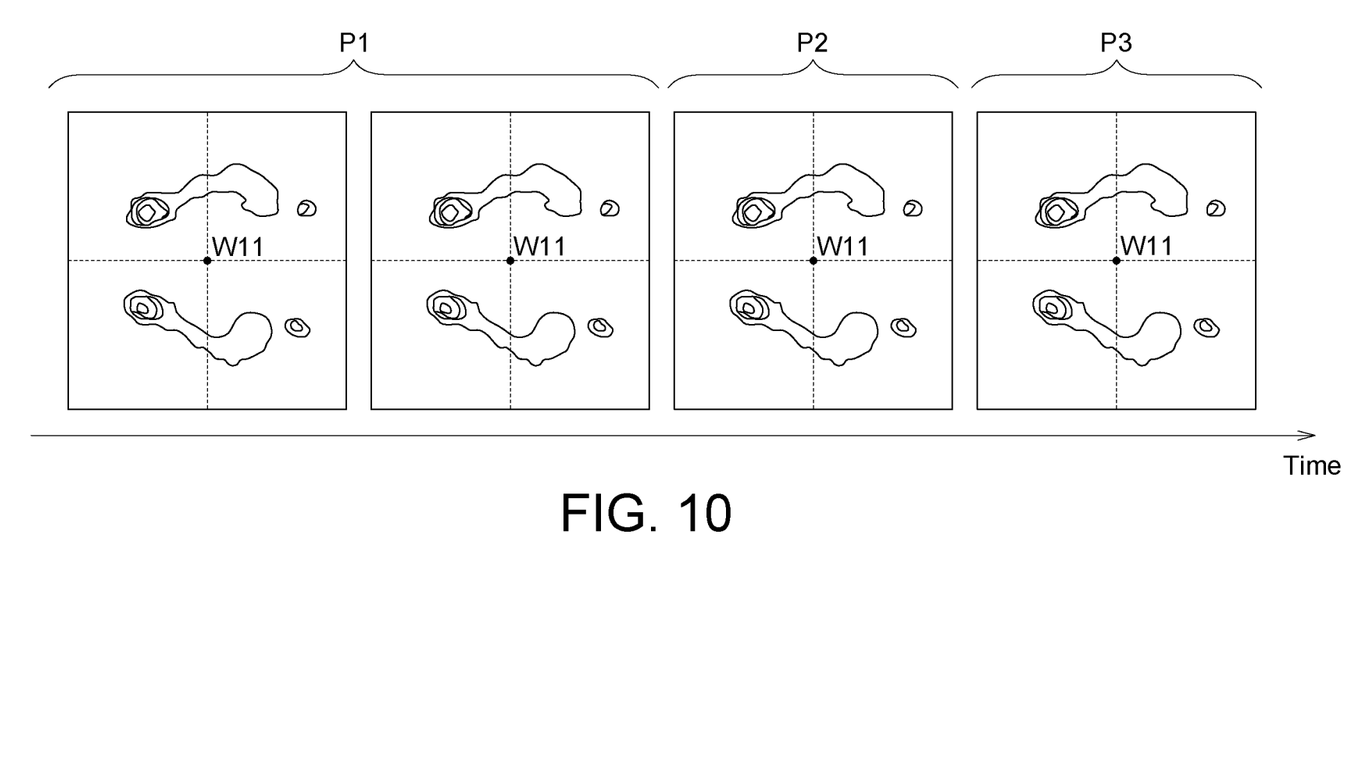
FIG. 10 is a distribution diagram showing continuous changes of foot pressure of a subject performing a squat exercise.

Refer to FIGS. 8 to 10. FIG. 8 is a flowchart of a movement assessing method according to another embodiment. FIG. 9 is a diagram showing continuous changes of limb position of a subject performing a squat exercise. FIG. 10 is a distribution diagram showing continuous changes of foot pressure of a subject performing a squat exercise. Steps S201 to S204 are similar to steps S101 to S104, and the similarities are not repeated here. The descriptions of the movement assessing method of the present embodiment start with step S206.

When the subject is performing a squat exercise, the movement can be divided into three phases P1, P2, and P3. At movement phase P1, the subject squats down. At movement phase P2, the subject maintains squat. At movement phase P3, the subject rises up. In step S206, the timing analysis unit 260 obtains multiple movement phases P1, P2, and P3 according to the change in the limb angles A11 and A12 and the change in the center of gravity W11, and analyzes a timing accuracy Gt1 according to the movement phases P1, P2, and P3. Refer to Table 3. The timing analysis unit 260 analyzes a ratio of the duration of the movement phase P1 to the sum of the durations of the movement phases P1, P2, and P3. In this step, the movement selection unit 110 selects a suggested range of time ratio RP1', such as 40-60%, from the database 160 according to the exercise selected by the subject. The timing analysis unit 260 checks whether the time ratio RP1 falls within the suggested range of time ratio RP1'. If yes, the timing accuracy Gt1 has 100 marks; otherwise, the timing accuracy Gt1 is progressively decreased according to the magnitude of deviation.

TABLE 3

| Time ratio | Suggested range of time ratio | Timing accuracy | Movement suggestion |
|---|---|---|---|
| RP1 | Suggested range of time ratio RP1': 40-60% | Gt1 | <40% The subject squats down too fast and needs to slow down. >60% The subject squats down too slow and needs to speed up. |

Then, the method proceeds to step S207, the index calculation unit 170 calculates the movement index via a limb weight Wa, a balance weight Wb and a timing weight Wt according to the limb position accuracy Ga1 and Ga2, the balance accuracy Gb1 and Gb2 and the timing accuracy Gt1. In this step, the movement selection unit 110 selects the limb weight Wa, the balance weight Wb and the timing weight Wt from the database 160 according to the exercise selected by the subject, and calculates a movement index IX2 according to formula (2). The sum of the limb weight Wa, the balance weight Wb and the timing weight Wt is equivalent to 1. The limb weight Wa, the balance weight Wb and the timing weight Wt are obtained according to the gender, the age or the movement type of the subject, different limb weights Wa, balance weights Wb and timing weights Wt can be assigned to different genders, ages or movement types.

$$IX2 = Wa \times Ga1 + Wa \times Ga2 + Wb \times Gb1 + Wb \times Gb2 + Wt \times Gt1 \quad (2)$$

Then, the method proceeds to step S208, the suggestion unit 180 provides a movement suggestion CM2 according to the limb position accuracy Ga1 and Ga2 and/or the balance accuracy Gb1 and Gb2, and the timing accuracy Gt1. For example, to simply check the correctness of a posture, the suggestion unit 180 provides a movement suggestion CM2 according to the limb position accuracy Ga1 and Ga2 and the timing accuracy Gt1 only. Or, to check whether the center of gravity changes according to the sequence of exercise, the suggestion unit 180 provides a movement suggestion CM2 according to the balance accuracy Gb1 and Gb2 and the timing accuracy Gt1 only. To simply check the accuracy of the force applied during exercise and related movement, the suggestion unit 180 provides a movement suggestion CM2 according to the limb position accuracy Ga1 and Ga2, the balance accuracy Gb1 and Gb2 and the timing accuracy Gt1. The contents of the movement suggestion CM2 are disclosed in Table 1, Table 2 and Table 3.

Figure 11:
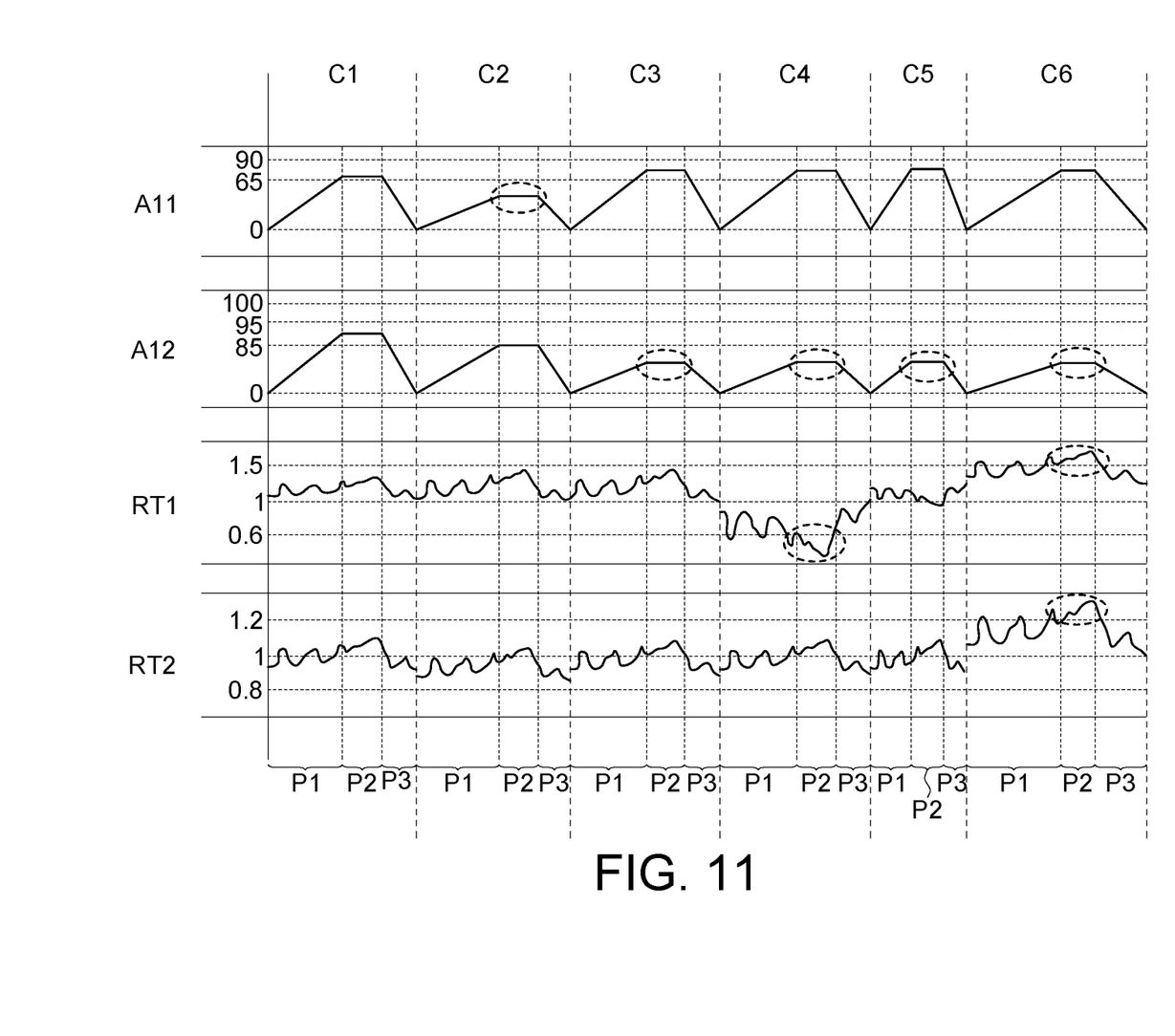
FIG. 11 exemplarily illustrates the movement suggestion for various situations.

The movement suggestions CM2 provided in various situations are exemplified in FIG. 11. In situation C1, during the movement phase P2, the limb angle A11 falls within the suggested range of limb angle A11', the limb angle A12 falls within the suggested range of limb angle A12', the front-and-back ratio RT1 falls within the suggested range of front-and-back ratio RT1', and the left-and-right ratio RT2 falls within the suggested range of left-and-right ratio RT2'.

Therefore, the movement suggestion CM2 provided in situation C1 is "Movement correct."

In situation C2, during the movement phase P2, the limb angle A11 is lower than the suggested range of limb angle A11'. Therefore, the movement suggestion CM2 provided in situation C2 is "Lean forward less."

In situation C3, during the movement phase P2, the limb angle A12 is lower than the suggested range of limb angle A12'. Therefore, the movement suggestion CM2 provided in situation C3 is "Squat depth not reached."

In situation C4, during the movement phase P2, the limb angle A12 is lower than the suggested range of limb angle A12', and the front-and-back ratio RT1 is lower than the suggested range of front-and-back ratio RT1'. Therefore, the movement suggestion CM2 provided in situation C4 is "Squat depth not reached and the body center of gravity needs to move backward."

In situation C5, during the movement phase P2, the limb angle A12 is lower than the suggested range of limb angle A12', and the duration of the movement phase P1 is too short, so that the time ratio RP1 is lower than the suggested range of time ratio RP1'. Therefore, the movement suggestion CM2 provided in situation C5 is "Squat depth not reached and squatting too fast."

In situation C6, during the movement phase P2, the limb angle A12 is lower than the suggested range of limb angle A12', the front-and-back ratio RT1 is lower than the suggested range of front-and-back ratio RT1', the left-and-right ratio RT2 is lower than the suggested range of left-and-right ratio RT2', and the duration of the movement phase P1 is too long, so that the time ratio RP1 is higher than the suggested range of time ratio RP1'. Therefore, the movement suggestion CM2 provided in situation C6 is "Squat depth not reached, the center of gravity needs to move backward and leftward, and squatting too slow."

Then, the method proceeds to step S209, the energy consumption calculation unit 190 calculates an estimated energy consumption EG2 according to the limb angles A11 and A12, the center of gravity W11 and the time ratio RP1.

Based on the above embodiments, in the absence of the coach or the physiotherapist, the subject still can obtain correct instructions of exercise and accordingly perform effective and safe autonomous exercise or self-rehabilitation.

While the invention has been described by way of example and in terms of the preferred embodiment(s), it is to be understood that the invention is not limited thereto. On the contrary, it is intended to cover various modification and similar arrangements and procedures, and the scope of the appended claims therefore should be accorded the broadest interpretation so as to encompass all such modification and similar arrangements and procedures.

What is claimed is:

1. A movement assessing method, comprising:
    obtaining at least one limb angle;
    analyzing a limb position accuracy according to the limb angle;
    obtaining a user's center of gravity;
    analyzing a balance accuracy according to the user's center of gravity; and
    calculating a movement index, wherein the movement index is a sum of at least a product of a limb weight and the limb position accuracy and a product of a balance weight and the balance accuracy.

2. The movement assessing method according to claim 1, wherein the limb weight and the balance weight are obtained according to the gender, the age or the movement type of a subject.

3. The movement assessing method according to claim 1, further comprising:
    providing a movement suggestion according to the limb position accuracy.

4. The movement assessing method according to claim 1, further comprising:
    providing a movement suggestion according to the balance accuracy.

5. The movement assessing method according to claim 1, further comprising:
    calculating an estimated energy consumption according to at least the limb angle and the user's center of gravity.

6. The movement assessing method according to claim 1, further comprising:
    obtaining a plurality of movement phases according to the change in the limb angle and the change in the user's center of gravity;
    analyzing a timing accuracy according to the movement phases.

7. The movement assessing method according to claim 6, wherein in the step of calculating the movement index, the movement index is a sum of the product of the limb weight and the limb position accuracy, the product of the balance weight and the balance accuracy and, a product of a timing weight and the timing accuracy.

8. The movement assessing method according to claim 7, wherein the sum of the limb weight, the balance weight and the timing weight is equivalent to 1.

9. The movement assessing method according to claim 7, wherein the balance weight is larger than the limb weight, and the limb weight is larger than the timing weight.

10. The movement assessing method according to claim 6, further comprising:
    calculating the estimated energy consumption according to the limb angle, the user's center of gravity and the movement phases in the step of calculating the estimated energy consumption.

11. A movement assessing system, comprising:
    an angle arithmetic unit for obtaining at least one limb angle;
    a limb analysis unit for analyzing a limb position accuracy according to the limb angle;
    a center of gravity arithmetic unit for obtaining a user's center of gravity;
    a balance analysis unit for analyzing a balance accuracy according to the user's center of gravity; and
    an index calculation unit for calculating a movement index, wherein the movement index is a sum of at least a product of a limb weight and the limb position accuracy and a product of a balance weight and the balance accuracy.

12. The movement assessing system according to claim 11, wherein the limb weight and the balance weight are obtained according to the gender, the age or the movement type of a subject.

13. The movement assessing system according to claim 11, further comprising:
    a suggestion unit for providing a movement suggestion according to the limb position accuracy.

14. The movement assessing system according to claim 11, further comprising:
    a suggestion unit for providing a movement suggestion according to the balance accuracy.

15. The movement assessing system according to claim 11, further comprising:
   an energy consumption calculation unit for calculating an estimated energy consumption according to at least the limb angle and the user's center of gravity.

16. The movement assessing system according to claim 11, further comprising:
   a timing analysis unit for obtaining a plurality of movement phases according to the change in the limb angle and the change in the user's center of gravity, and for analyzing a timing accuracy according to the movement phases.

17. The movement assessing system according to claim 16, wherein the movement index is a sum of the product of the limb weight and the limb position accuracy, the product of the balance weight and the balance accuracy and, a product of a timing weight and the timing accuracy.

18. The movement assessing system according to claim 17, wherein the sum of the limb weight, the balance weight and the timing weight is equivalent to 1.

19. The movement assessing system according to claim 17, wherein the balance weight is larger than the limb weight, and the limb weight is larger than the timing weight.

20. The movement assessing system according to claim 16, wherein the energy consumption calculation unit calculates the estimated energy consumption according to the limb angle, the user's center of gravity and the movement phases.

* * * * *